United States Patent
Hughes et al.

(10) Patent No.: US 6,364,519 B1
(45) Date of Patent: Apr. 2, 2002

(54) BONE CEMENT SYSTEM

(75) Inventors: Christopher P. Hughes, Cordova; Richard A. Rocco, Collierville, both of TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 09/669,611

(22) Filed: Sep. 26, 2000

(51) Int. Cl.[7] .................. B65D 71/00; B65D 69/00; B01F 15/00
(52) U.S. Cl. .................. 366/130; 366/189; 220/221; 220/222; 220/557; 220/568
(58) Field of Search .................. 206/223, 568, 206/221, 222, 557; 366/130, 139, 189, 150.1; 220/513, 517, 359.1, 359.2, 669; D9/347

(56) References Cited

U.S. PATENT DOCUMENTS

| | | | |
|---|---|---|---|
| 3,083,821 A | * | 4/1963 | Woodson |
| 3,756,571 A | * | 9/1973 | Winberg |
| 4,277,184 A | * | 7/1981 | Solomon |
| 4,294,349 A | * | 10/1981 | Ibsen et al. |
| 4,341,302 A | * | 7/1982 | Baker et al. |
| 4,364,473 A | * | 12/1982 | Bogaert |
| D280,290 S | * | 8/1985 | Bakus |
| 4,673,085 A | * | 6/1987 | Badouard et al. |
| 5,203,459 A | * | 4/1993 | Wade |
| 5,333,737 A | * | 8/1994 | Clark |
| 6,003,673 A | * | 12/1999 | Vieu |

OTHER PUBLICATIONS

Palacos R Radiopaque bone cement packaging (Cat. No. 12–0001)(Smith & Nephew) (undated).
VersaBond™ Radiopaque bone cement packaging (No. 7127–1140) (Smith & Nephew) (undated).
VersaBond™ with Gentamicin Radiopaque Polymer Powder packaging (Smith & Nephew) (undated).
VersaBond™ Medium Viscosity Cement "The Bond Between Strength and Versatility," brochure (Smith & Nephew) (Jan. 2000).
Mix O.R.™ Vacuum Mixing System with Cartridge and Nozzle Packaging (Smith & Nephew (undated).

* cited by examiner

Primary Examiner—Tony G. Soohoo
(74) Attorney, Agent, or Firm—Kilpatrick Stockton LLP

(57) ABSTRACT

A relatively rigid container for packaging bone cement powder. The container is filled with the powder and then sealed with a lid. To access the powder, the nurse simply peels back the lid. Because no tearing or cutting open is required as with the current pouches used to store cement powder, the likelihood of powder loss and contamination is reduced and the quality of the resulting cement thereby enhanced. The container may be shaped to guide and/or mate with a funnel that guides the powder into the mixing chamber of the cement mixer. Additionally, the container may be shaped to allow for actual mixing of the powder and the liquid within the container. The liquid monomer is then simply added to the powder already in the container, drastically reducing the risk of powder loss.

20 Claims, 3 Drawing Sheets

BONE CEMENT SYSTEM

FIELD OF THE INVENTION

This invention relates generally to a bone cement system comprising a contoured cement powder storage container with a peel-off lid that facilitates safe and efficient access to the powder and an ampoule containing liquid monomer for combining with the cement powder to prepare the cement.

BACKGROUND OF THE INVENTION

Bone cement is prepared by mixing liquid monomer with cement powder. Such preparation must occur under sterilized conditions. To accomplish this, current powders are sterilized and packaged in a sealed pouch. The liquid is generally packaged in a glass ampoule. The pouch and ampoule are then packaged together and remain unopened until needed in the sterilized environment of the operating room.

The pouch and the ampoule hold the precise amounts of their respective cement components so that the nurse simply may combine the components in their pre-measured amounts to produce cement having optimum characteristics. To prepare the cement, a nurse opens the pouch by tearing or cutting the pouch with scissors or a scalpel blade and pours the powder into the mixing chamber of a cement mixer. The liquid is then mixed with the powder to produce the cement for use in surgery.

This technique can be both dangerous and inefficient, as well as jeopardize the quality of the resulting cement. The nurse, when using a knife or blade to open the pouch, may cut herself and, unbeknownst to her, contaminate the powder. Moreover, when tearing or cutting open the pouch, the pouch may be opened too forcefully or the pouch opening may be made too large, resulting in powder spilling from the pouch and consequent contamination of the powder. Finally, because the pouch provides no spout or other channel for guiding the powder, powder loss also occurs when attempting to pour the powder from the pouch into the mixing chamber.

In addition to possible waste of cement powder, the current packaging may also result in the loss of the liquid. When the pouch and ampoule are packaged together, the ampoule is generally not well secured in the packaging. In the operating room, nurses typically dump the contents out of the packaging and onto a tray. This can result in breakage of the fragile glass ampoule containing the liquid.

Because the pouch and the ampoule each contain the precise amount of a cement component (powder or liquid) for combination with the other cement component (liquid or powder), loss of an amount of either component compromises the desired powder/liquid ratio. The nurse is forced to guess how much of the un-spilled component to combine with the remnants of the spilled component to regain the desired ratio and thereby obtain the desired consistency of the cement.

SUMMARY OF THE INVENTION

The present invention addresses the above-described problems inherent in current packaging practices by providing a relatively rigid container for packaging the cement powder. The container is filled with the powder and then sealed with a lid. To access the powder, the nurse simply peels back the lid. Because no tearing or cutting is required as with the current pouches, the likelihood of powder loss and contamination is reduced. The container may be shaped to guide and/or mate with a funnel that guides the powder into the mixing chamber of the cement mixer. Additionally, the container may be shaped to allow for actual mixing of the powder and the liquid within the container. The liquid monomer is then simply added to the powder already in the container, drastically reducing the risk of powder loss and consequent detrimental effects.

It is an object of the present invention to provide a cement powder storage container that is safer to open than existing storage containers, thereby reducing the risk of powder contamination.

It is another object of the present invention to provide a cement powder storage container that is easier to open than existing storage containers, thereby reducing the risk of powder waste when opening of the container.

It is still another object of the present invention to provide a cement powder storage container that facilitates precise pouring of the powder from the container to reduce the risk of powder waste when dispensing the powder from the container.

It is a further object of the present invention to provide a cement powder storage container in which the powder and liquid monomer may be mixed.

DETAILED DESCRIPTION OF THE DRAWINGS

Figure 1:
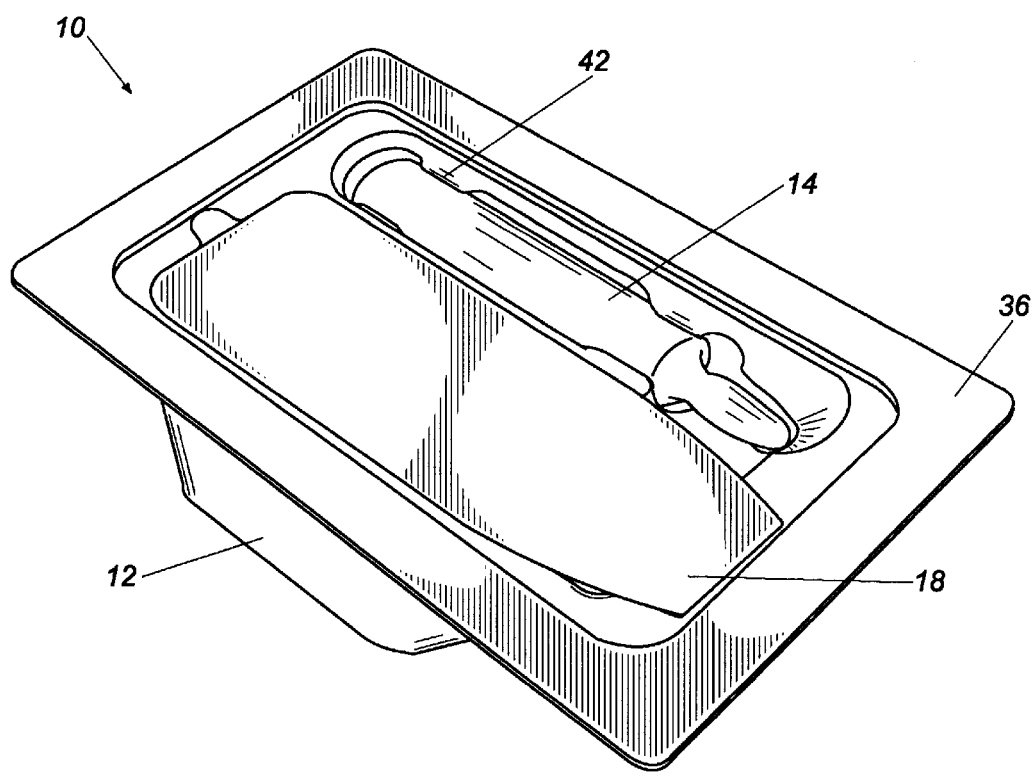
FIG. 1 is a perspective view of one embodiment of the bone cement system of the present invention, wherein the cement powder container and the liquid monomer ampoule are seated in a tray.

FIG. 1 illustrates an embodiment of the bone cement system 10 according to the present invention. System 10 comprises a cement powder container 12 and a liquid monomer ampoule 14. The container 12 may be made from any material possessing suitable physical properties including structural integrity and relative rigidity, but is preferably made from plastic. The container 12 may be molded in a variety of shapes that facilitate either pouring of the cement powder into the mixing chamber of a cement mixer, such as a MixOR Vacuum Mixing System, or mixing of liquid with the powder already in the container 12.

Figure 2:
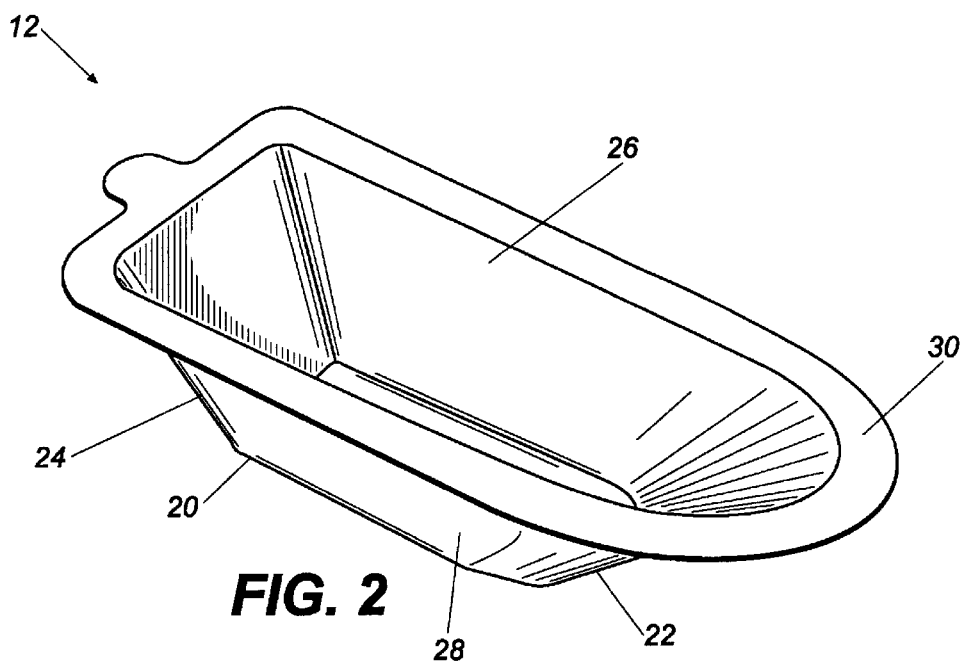
FIG. 2 is a perspective view of one embodiment of the container of the present invention.
Figure 5:
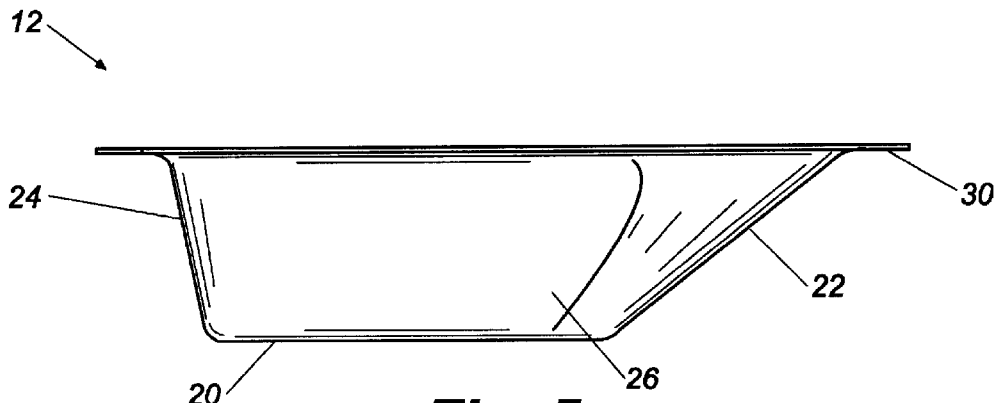
FIG. 5 is a side elevation view of the container of FIG. 2.

In the embodiment shown in FIGS. 2 and 5, the container 12 is shaped like an upside-down iron and has a bottom 20, a front wall 22, a back wall 24, and side walls 26, 28. A top rim 30 extends outwardly from the walls 22, 24, 26, 28. The front wall 22 slants upwardly from the bottom 20 of the container 12. Moreover, the side walls 26, 28 taper towards each other proximate to the front wall 22. This slanting and tapering configuration helps guide the powder as it exits the container 12 and into the mixing chamber. Once again, however, the container 12 may assume a number of alternative shapes that serve to guide the powder from the container 12 and is not limited to this disclosed embodiment.

Figure 6:
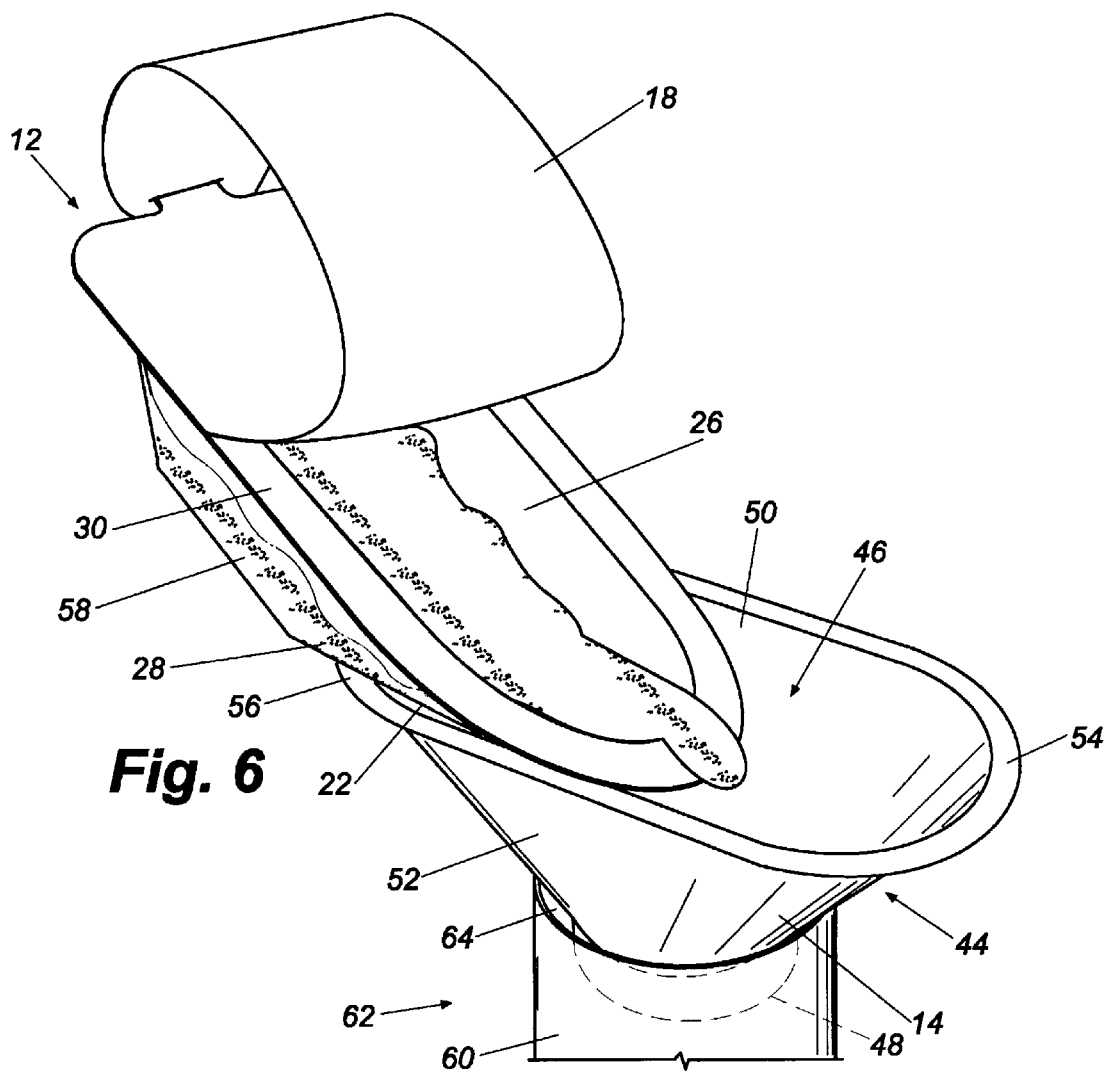
FIG. 6 is a perspective view of one embodiment of a system for mixing cement, wherein the embodiment of FIG. 4 mates with a funnel and the funnel mates with a cement mixer.

The container 12 may also be shaped to mate with existing funnels that further enhance the pouring precision. Mating of the container with one type of funnel is shown in FIG. 6, but a variety of differently-shaped funnels could be used. Funnel 44 has an input end 46 and an output end 48. The input end 46 is preferably elongated, having two relatively straight sides 50, 52 and two curved ends 54, 56. The slanted front wall 22 and the tapered side walls 26, 28 of the container 12 mate with a curved end 54, 56. The funnel 44 is preferably narrow enough so that the sides 50, 52 of the funnel 44 contact either the side walls 26, 28 or the rim 30 of the container 12, thereby preventing lateral movement of the container 12 and ensuring that the powder 58 is directed into the funnel 44. The output end 48 of the funnel 44 mates with an opening 64 of a cement mixer 62 (not shown in its entirety), such as a MixOR vacuum mixing system, to guide the powder into the mixing chamber 60 of the mixer 62. The container 12 may also serve as the chamber in which the powder and liquid can be mixed and therefore may not require any tapering or slanting or other means for guiding the powder from the container 12.

Figure 3:
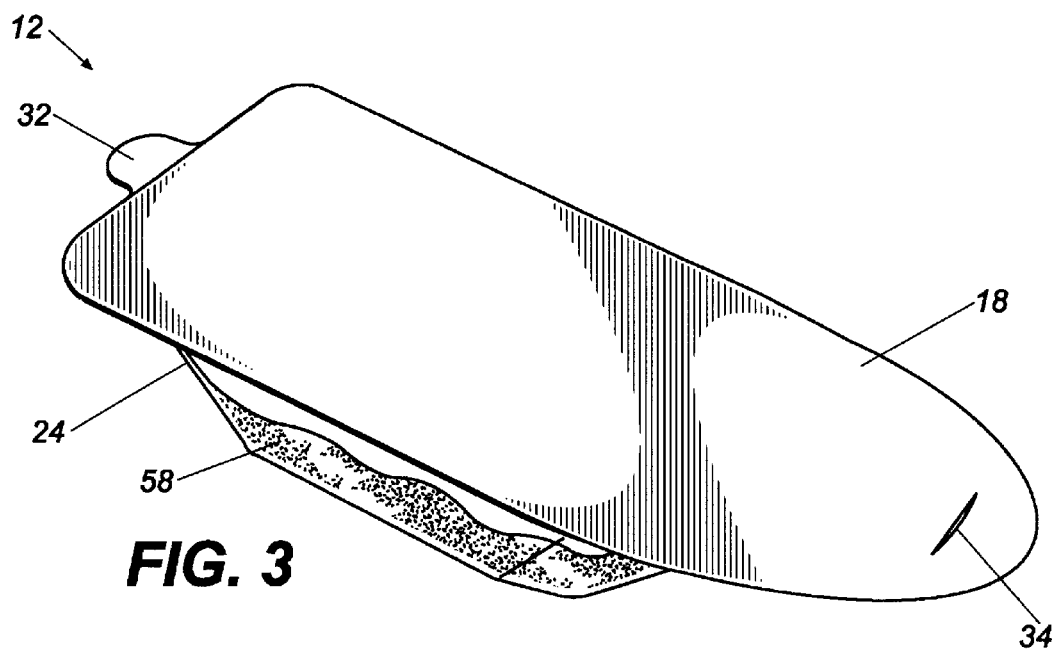
FIG. 3 is a perspective view of one embodiment of the container of the present invention, wherein the container of FIG. 2 is covered by a lid.
Figure 4:
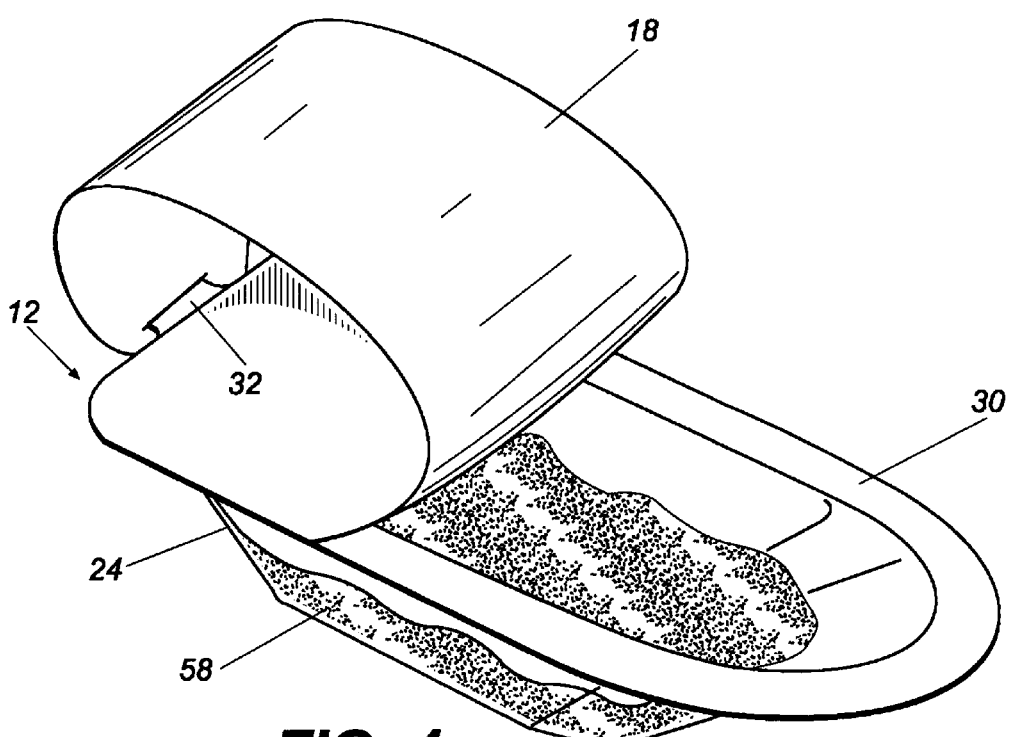
FIG. 4 is another perspective view of the embodiment of FIG. 3, wherein the lid is peeled back from the container.

A lid 18 is secured to the container 12 (for example, to the rim of the container (assuming the container has a rim), as shown in FIGS. 3 and 4), thereby covering and securing the sterilized powder 58 within the container 12. The lid 18 may be made from any material possessing suitable physical properties including structural integrity and water-, puncture-, tear-, and abrasion-resistance. Tyvek® possesses these desired properties. The lid 18 is preferably secured to the container 12 with an adhesive having a strength sufficient to retain the lid 18 on the container 12 during storage but which still allows for the lid 18 to be peeled easily away from the container 12. The lid 18 may be peeled back partially from or entirely off of the container 12 to expose the powder.

The container 12 is preferably, but does not have to be, equipped with a tab 32 extending outwardly from the container 12. In the embodiment shown in FIGS. 3 and 4, the tab 32 extends from the rim 30 that extends outwardly from the back wall 24 of the container 12. Naturally, the tab 32 may also extend directly from a container wall. The lid 18 is preferably, but does not have to be, equipped with a slit 34 located in the lid 18 so that, when the lid 18 is covering the container 12, the slit 34 is positioned opposite to the tab 32. When the nurse pulls back the lid 18, she may slip the slit 34 over the tab 32 (see FIG. 4), thereby securing the lid 18 in place and preventing it from interfering during the dispensing of the powder, as shown in FIG. 6.

The bone cement system 10 may also contain a tray 36 for holding the container 12 and the ampoule 14 (see FIG. 1). The tray 36 may be made from any material possessing suitable physical properties including structural integrity and relative rigidity, but is preferably made from plastic. The tray 36 is preferably molded with a compartment for receiving the container 12 and with a compartment for receiving the ampoule 14. The compartment for receiving the ampoule 14 is equipped with one or more protrusions 42 so that the width of the compartment is less than the diameter of the ampoule 14 at least along a portion of the compartment. The width of the compartment at the protrusions(s) 42 should be narrow enough to prevent the ampoule 14 from falling out of the tray 36 and consequently breaking, but be wide enough to allow for insertion and removal of the ampoule 14 from the tray 36 with relative ease.

The foregoing is provided for the purpose of illustrating, explaining and describing embodiments of the present invention. Further modifications and adaptations to these embodiments will be apparent to those skilled in the art and may be made without departing from the spirit of the invention or the scope of the following claims.

What is claimed is:

1. A system for storing cement components comprising a container storing cement powder, and a lid, at least a portion of which is attached to the container and is capable of being peeled off the container to access the powder in the container, wherein the container has a bottom and at least one wall connected to the bottom, at least a portion of said wall slanting upwardly from the bottom.

2. The system of claim 1, wherein the container comprises plastic.

3. The system of claim 1, wherein the at least a portion of the lid is attached to the container with adhesive.

4. The system of claim 1, wherein the container further comprises a rim extending outwardly from the at least one wall.

5. The system of claim 4, wherein the at least a portion of the lid is attached to the rim of the container.

6. The system of claim 1, wherein the container further comprises a tab extending outwardly from the at least one wall.

7. The system of claim 6, further comprising a slit in the lid for engaging the tab.

8. The system of claim 1, wherein the at least one wall comprises a front wall, a back wall, and two side walls, wherein the front wall slants upwardly from the bottom and at least a portion of at least one of the side walls tapers towards the other side wall proximate to the front wall.

9. The system of claim 1, further comprising an ampoule containing a liquid monomer.

10. The system of claim 9, wherein the ampoule comprises glass.

11. The system of claim 1, wherein the container is adapted to mate with a funnel.

12. A system for storing cement components comprising:
  a) a plastic container storing cement powder comprising a bottom, a front wall, a back wall, and two side walls, a rim extending outwardly from at least one of the walls and a tab extending outwardly from at least one of the walls, wherein all of the walls are connected to the bottom, the front wall slants upwardly from the bottom and at least a portion of at least one of the side walls tapers towards the other side wall proximate to the front wall;
  b) a lid having a slit for engaging the tab, wherein the lid is adhesively attached to the container and capable of being peeled at least partially from the container to expose the powder in the container; and
  c) a glass ampoule containing a liquid monomer.

13. A method for storing cement components comprising:
  a) inserting cement powder into a container comprising a closed bottom and at least one wall connected to the bottom, at least a portion of said wall slanting upwardly from the bottom; and
  b) attaching a lid to at least a portion of the container to seal the powder into the container.

14. A method for making cement comprising:
  a) providing a container storing cement powder and having a lid, at least a portion of said lid being attached to the container and capable of being peeled off the container to access the powder in the container, wherein the container has a closed bottom and at least one wall connected to the bottom, at least a portion of said wall slanting upwardly from the bottom;

b) peeling the lid at least partially from the container;

c) pouring the cement powder into a mixing bowl;

d) mixing a liquid monomer with the cement powder in the mixing bowl.

15. The method of claim 14, further comprising inserting a tab extending from one end of the container into a slit located in the lid at an opposing end of the container to secure the lid in place.

16. The method of claim 14, wherein the pouring of the cement powder into the mixing bowl further comprises guiding the powder from the container and into the mixing bowl using a funnel.

17. A system for mixing cement comprising:

a. a cement mixer having a mixing chamber with an opening;

b. a funnel member having an input end and an output end, wherein the output end mates with the opening of the mixer; and c. a container storing cement powder, and a lid, at least a portion of which is attached to the container and is capable of being peeled off the container to access the powder in the container, wherein the container is adapted to mate with the input end of the funnel member.

18. The system of claim 17, wherein the container further comprises a tapered end to mate with the input end of the funnel member.

19. The system of claim 18, wherein the container further comprises a bottom, a front wall and two side walls, wherein the front wall slants upwardly from the bottom and at least a portion of at least one of the side walls tapers towards the other side wall proximate to the front wall to form the tapered end.

20. The system of claim 17, further comprising an ampoule containing a liquid monomer.

\* \* \* \* \*

Adverse Decision in Interference

Patent No. 6,364,519, Christopher P. Hughes, Richard A. Rocco, BONE CEMENT SYSTEM, Interference No. 105,160, final judgment adverse to the patentees rendered, July 15, 2004 as to claims 1-6, 8-11, 13-14, 16-20.

*(Official Gazette December 7, 2004)*